United States Patent [19]

Ono et al.

[11] Patent Number: 4,825,003
[45] Date of Patent: Apr. 25, 1989

[54] PRODUCTION PROCESS OF 2-CHLOROPROPIONALDEHYDE

[75] Inventors: Hiroshi Ono, Fujisawa; Takaharu Kasuga, Kamakura; Shinji Kiyono, Yokohama; Yoshihiro Fujita, Kamakura, all of Japan

[73] Assignee: Mitsui Toatsu Chemicals, Incorporated, Tokyo, Japan

[21] Appl. No.: 95,218

[22] Filed: Sep. 11, 1987

[30] Foreign Application Priority Data

Sep. 17, 1986 [JP] Japan ................... 61-217301
Jul. 3, 1987 [JP] Japan ................... 62-165439
Jul. 8, 1987 [JP] Japan ................... 62-168566

[51] Int. Cl.$^4$ .................................. C07C 45/50
[52] U.S. Cl. ..................... 568/490; 568/454; 568/466
[58] Field of Search ............ 568/454, 490, 466, 455

[56] References Cited

U.S. PATENT DOCUMENTS 4,593,126  6/1986  Cornils et al. ............ 568/454
4,654,445  3/1987  Ono et al. ................ 568/454

FOREIGN PATENT DOCUMENTS 0157316  3/1985  European Pat. Off. ............ 568/454
0163234  5/1985  European Pat. Off. ............ 568/454
1397779  8/1965  France .
0161340  12/1981  Japan ................................ 568/490
126046  6/1986  Japan .
10038  1/1987  Japan .
22738  1/1987  Japan .
96444  5/1987  Japan .

OTHER PUBLICATIONS

Helvetica Chimica Acta, 48 (5), 1151–1157.

Primary Examiner—Werren B. Lone
Attorney, Agent, or Firm—Fisher, Christen & Sabol

[57] ABSTRACT

A process for the production of 2-chloropropionaldehyde from vinyl chloride, carbon monoxide and hydrogen which comprises using a rhodium compound and a trivalent organic phosphorus compound or the oxide of a trivalent organic phosphorus compound as a catalyst and carrying out the reaction under the co-existence of an acid the pka of which is in the range of 0.5–5, the oxide, hydroxide or a weak acid salt of an alkali metal or alkaline earth metal, or a buffer solution.

12 Claims, No Drawings

PRODUCTION PROCESS OF 2-CHLOROPROPIONALDEHYDE

BACKGROUND OF THE INVENTION (a) Field of the Invention

This invention relates to a process for the production of 2-chloropropionaldehyde from vinyl chloride, carbon monoxide and hydrogen as raw materials.

(b) Description of the Prior Art

2-Chloropropionaldehyde can find applications as useful intermediates for chemicals, agricultural chemicals and medicines. It has been known to produce this compound from vinyl chloride, carbon monoxide and hydrogen as raw materials, as disclosed, for example, in French Pat. No. 1,397,779 and HELVETICA CHIMICA ACTA, 48(5), 1151–1157. All of these processes employ cobalt carbonyl as a catalyst. In French Pat. No. 1,397,779 referred to above, for example, the raw materials are reacted for 90 minutes under the conditions of a reaction temperature of 110° C. and a reaction pressure of 200 atm., thereby obtaining reaction results of a vinyl chloride conversion of 57.4% and a selectivity toward 2-chloropropionaldehyde of 86.2%.

However, these processes which employ cobalt carbonyl as a catalyst require cobalt carbonyl in a large amount and a reaction pressure as high as 160–200 atm. because the catalytic activity of catalyst per unit amount of cobalt is extremely low. Moreover, the reaction is carried out at a reaction temperature of 75°–125° C. for 90–120 minutes.

The intended product, 2-chloropropionaldehyde, is a thermally-unstable material. Under the conditions of such a reaction temperature and reaction time, a substantial portion of 2-chloropropionaldehyde is consumed through a consecutive reaction and the reaction yield is thus reduced. Accordingly, these processes have poor reproducibility.

Further, hydrogen chloride is by-produced through the consecutive reaction or other side reactions. It causes the materials of reactor to suffer severe corrosion and it reacts with the cobalt carbonyl catalyst to form cobalt chloride. Therefore, the processes involve problems of developing an obstacle to the reutilization of the catalyst.

As improved processes in these disadvantages, the present inventors have found processes in which vinyl chloride, carbon monoxide and hydrogen are reacted in the presence of a rhodium compound and a base as disclosed in Japanese Patent Laid-Open Nos. 126046/1986, 10038/1987, 22738/1987 and 96444/1987. In accordance with these processes, the reaction proceeds at lower temperatures and pressures than in the conventional processes which employ cobalt carbonyl as a catalyst and a sufficient selectivity can be attained toward the intended product.

In these processes, a combination of a compound represented by the general formula $P(R^1R^2R^3)$ wherein P denotes a phosphorus atom and $R^1$, $R^2$, and $R^3$ represent individually an alkyl, aryl, cycloalkyl, alkoxy, aryloxy or cycloalkoxy group and a nitrogen-containing compound the pka of which is in the range of 3–11 may preferably be used as the base in the presence or absence of water.

Among these nitrogen-containing compounds having pka levels of 3–11, pyridine compounds, quinoline compounds, imidazole compounds and morpholine compounds are used particularly favorably in view of reaction results and other aspects. All of these bases are comparatively expensive compounds. Therefore, it is necessary to minimize the loss occurring upon their industrial use by providing, for example, with a recovery apparatus of these bases.

Further, all of these compounds are highly reactive so that they are consumed, though slowly, when they are used for a prolonged period of time. It is therefore necessary to conduct the operation in such a manner as to prevent the loss to greatest possible extent. The conditions of the operation however do not necessarily agree with the conditions which are favorable to the synthesis of 2-chloropropionaldehyde. Accordingly, the processes involve problems in that the reaction under the conditions with a little deviation from the optimum synthesis conditions as well as the loss exerts considerable influences on the production cost of the intended product, 2-chloropropionaldehyde.

Further, there are many compounds which have vapor pressures among the pyridine compounds, quinoline compounds and morpholine compounds. These compounds are disadvantageous in that they are admixed into the reaction product of 2-chloropropionaldehyde, though in small amounts, upon separation of 2-chloropropionaldehyde from the reaction solution through distillation, thereby not only degrading the purity of the product of 2-chloropropionaldehyde but also interfering with oxidation reaction seriously upon the production of 2-chloropropionic acid by oxidizing 2-chloropropionaldehyde.

SUMMARY OF THE INVENTION

An object of the present invention is to provide a process for the production of 2-chloropropionaldehyde with a high selectivity at a low temperature and pressure from vinyl chloride, carbon monoxide and hydrogen.

Another object of the present invention is to provide a process for the production of 2-chloropropionaldehyde in a simple apparatus without need for any particular use of the conditions for preventing the loss of the base used as a catalyst or the means for the recovery of the base.

A further object of the present invention is to provide a process for the production of 2-chloropropionaldehyde containing impurities that obstruct oxidation such as amines in only a very small amount.

The above objects of the present invention are achieved by the following production process of 2-chloropropionaldehyde:

In a process for the production of 2-chloropropionaldehyde by reacting vinyl chloride, carbon monoxide and hydrogen in the presence of a rhodium compound and a trivalent organic phosphorus compound or the oxide of a trivalent organic phosphorus compound, the improvement which comprises carrying out the reaction under the co-existence of:

(1) at least one acid the pka of which is in the range of 0.5–5, (2) at least one compound selected from the oxide, hydroxide and weak acid salts of an alkali metal or an alkaline earth metal, or (3) a buffer solution.

DETAILED DESCRIPTION OF THE PREFERRED EMBODIMENTS

In the production process of 2-chloropropionaldehyde of the present invention, reaction proceeds according to the following reaction formula:

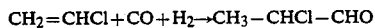

$$CH_2=CHCl + CO + H_2 \rightarrow CH_3-CHCl-CHO$$

As rhodium compounds useful in the practice of the process of the present invention, there are the oxide, mineral acid salts and organic acid salts of rhodium as well as rhodium complex compounds. As preferred examples of such rhodium compounds, may be mentioned rhodium oxide, rhodium nitrate, rhodium sulfate, rhodium acetate, triacetylacetonatorhodium, dicarbonylacetylacetonatorhodium, dodecacarbonyltetrarhodium and hexadecacarbonylhexarhodium.

In addition to these compounds, complex compounds formed of the rhodium compound and a base may be used more preferably as rhodium complex compounds. The base may include trivalent organic phosphorus compounds or the oxides of trivalent organic phosphorus compounds which are used favorably in the process of the present invention, but other bases may also be used. As exemplary complex compounds, may be mentioned, for example, hydridocarbonyl-tris(triphenylphosphine)rhodium [RhH(CO)(PPh$_3$)$_3$], nitrosyl-tris(triphenylphosphine)rhodium [Rh(NO)(PPh$_3$)$_3$] and $\eta$-cyclopentadienylbis(triphenylphosphine)rhodium [Rh(C$_5$H$_5$)(PPh$_3$)$_2$].

In the process of the present invention, the above-described rhodium compound may be used in an equivalent amount in the range of 0.0001–1,000 milligram atoms or preferably 0.001–100 milligram atoms in terms of rhodium atom per liter of the liquid phase in the reaction system. Further, the aforesaid trivalent organic phosphorus compound or oxide of the trivalent organic phosphorus compound used in the process of the present invention may be used individually in an amount in the range of 0.1–500 moles or preferably 0.5–100 moles per gram atom of rhodium.

The trivalent organic phosphorus compound and the oxide of the trivalent organic phosphorus compound useful in the practice of the process of the present invention are illustrated as follows:

As the trivalent organic phosphorous compound may be mentioned a trivalent organic phosphorus compound represented by the general formula P(R$^1$R$^2$R$^3$) wherein P denotes a phosphorus atom and R$^1$, R$^2$ and R$^3$ represent individually the same or different alkyl, aryl, cycloalkyl, alkoxy, aryloxy or cycloalkoxy group. Specific examples of the trivalent organic compound may embrace phosphines such as trimethylphosphine, triethylphosphine, tripropylphosphine, tributylphosphine, trioctylphosphine, triphenylphosphine, tricyclohexylphosphine and tribenzylphosphine and phosphites such as trimethylphosphite, triethylphosphite, tripropylphosphite, tributylphosphite, trioctylphosphite, triphenylphosphite, tricyclohexylphosphite and tribenzylphosphite.

As particular phosphines, besides those represented by the aforesaid general formula P[R$^1$R$^2$R$^3$], may favorable be used diphosphines such as bisdiphenylphosphinomethane and bisdiphenylphosphinoethane and phosphines bonded to crosslinking polystyrene.

Illustratives of the oxides of trivalent organic phosphorus compounds may include alkylphosphine oxides such as triethylphosphine oxide, tributylphosphine oxide and trioctylphosphine oxide, arylphosphine oxides such as triphenylphosphine oxide and tritolylphosphine oxide, and alkyl-arylphosphine oxides which contain both of alkyl and aryl groups. In addition, alkyl- or arylphosphite oxides such as triethylphosphite oxide, tributylphosphite oxide and triphenylphosphite oxide and alkyl-arylphosphite oxides which contain both of alkyl and aryl groups may also be used. Further, the oxides of multidentate phosphines such as bis-1,2-diphenylphosphinomethane dioxide may be used as well.

As the acid the pka of which is in the range of 0.5–5 and which is useful in the practice of the present invention may be mentioned a variety of organic acids and inorganic acids. By using such an acid, the aforesaid catalysts composed of rhodium and a base can exhibit high activities and moreover long stable operation becomes possible in the production of 2-chloropropionaldehyde without encountering the above-described various problems of the prior art processes. At the same time, the number of regeneration times of the catalyst solution can also be reduced so that the loss of expensive rhodium used as a catalyst can be decreased as well.

In the process of the present invention, carboxylic acids may preferably be used as such an acid. Specific examples of carboxylic acids may include saturated or unsaturated aliphatic mono- or polycarboxylic acids such as formic acid, acetic acid, propionic acid, butyric acid, isobutyric acid, heptanoic acid, acrylic acid, methacrylic acid, crotonic acid, oxalic acid, malonic acid, methylmalonic acid, succinic acid, adipic acid, maleic acid, fumaric acid and 1,2,3-propanetricarboxylic acid, and monovalent or polyvalent aromatic carboxylic acids such as benzoic acid, toluic acid, o-ethylbenzoic acid, 2,4-dimethylbenzoic acid, phthalic acid, isophthalic acid, terephthalic acid, 3-methylphthalic acid, trimellitic acid, trimesic acid, pyromellitic acid, benzenepentacarboxylic acid and mellitic acid.

Further, carboxylic acids formed by bonding a substituent group such as a halogen atom or an amino or hydroxyl group to an alkyl or aryl group of the aforementioned carboxylic acids are also preferred. Illustratives of these carboxylic acids may include halogen-substituted aliphatic carboxylic acids such as monofluoroacetic acid, difluoroacetic acid, trifluoroacetic acid, monochloroacetic acid, dichloroacetic acid, trichloroacetic acid, monobromoacetic acid, dibromoacetic acid, 2-chloropropionic acid, 3-chloropropionic acid and 2,2-dichloropropionic acid, halogen-substituted aromatic carboxylic acids such as o-chlorobenzoic acid, m-chlorobenzoic acid, p-chlorobenzoic acid and o-fluorobenzoic acid, amino acids such as glycin, sarcosine, alanine, $\beta$-alanine, 4-aminobutyric acid, valine, serine, aspartic acid and glutamic acid and hydroxycarboxylic acids such as glycolic acid, lactic acid, 2-hydroxybutric acid, glyceric acid, malic acid, tartaric acid, citric acid, p-hydroxybenzoic acid, salicyclic acid and 2,4-dihydroxybenzoic acid.

Besides, carboxylic acids bonded with substituent groups other than those described above such as phenylacetic acid, pyruvic acid, anisic acid, o-nitrobenzoic acid and cinnamic acid are also mentioned as preferred examples. In the process of the present invention, halogen-substituted aliphatic carboxylic acids and monovalent or polyvalent aromatic carboxylic acids are used particularly preferably among the above-described carboxylic acids.

In the process of the present invention, phosphonic acids, phosphonous acids, phosphinic acids and phosphinous acids are also used preferably as the acid. Illustratives of these acids may include methylphosphonic acid, ethylphosphonic acid, phenylphosphonic acid, phenylphosphonous acid, dimethylphosphinic acid, diethylphosphinic acid, diphenylphosphinic acid and diphenylphosphinous acid.

In the process of the present invention, it is particularly preferable to conduct the reaction in the presence of water, as described below. At this time, cases where the aforesaid acids are supplied in the form of precursors which form the acids in the presence of water, for example, esters, acid chlorides or acid anhydrides are mentioned as a preferable embodiment of the process of the present invention. For example, esters such as ethyl acetate, methyl benzoate, dibutyl phthalate, phenylphosphonic acid diethyl ester and phenylphosphonous acid diethyl ester, acid chlorides such as acetyl chloride, benzoic acid chloride and diphenylphosphinous acid chloride, and acid anhydrides such as acetic anhydride, maleic anhydride and phthalic anhydride are illustrated.

The oxides, hydroxides and weak acid salts of alkali metals or alkaline earth metals useful in the practice of the process of the present invention may be mentioned specifically as follows:

As illustratives of the oxide of an alkali metal or alkaline earth metal may be mentioned sodium oxide, potassium oxide, calcium oxide and barium oxide, while the hydroxide of an alkali metal or alkaline earth metal may include, for example, sodium hydroxide, potassium hydroxide, calcium hydroxide and barium hydroxide.

As illustratives of the weak acid salts of an alkali metal or alkaline earth metal may be mentioned carbonates or hydrogencarbonates such as sodium carbonate potassium carbonate and calcium hydrogencarbonate, and carboxylic acid salts such as sodium acetate, potassium acetate, calcium acetate, sodium formate, potassium formate, sodium propionate, sodium benzoate, potassium citrate, sodium ascorbate, sodium monochloroacetate and sodium dichloroacetate. In addition, compounds of alkali metal or alkaline earth metals which exhibit alkaline properties in water, for example, trisodium phosphate may also be included in the preferred salts in the practice of the process of the present invention.

The buffer solution in the process of the present invention means a solution having a buffer function to pH-varying factors and is generally prepared by dissolving a proper combination of an acid, base and various salts in a solvent. For the buffer solution, it is necessary to select the kinds of acid and base constituting the buffer solution and the concentrations and mixing ratio of these constituents in accordance with the intended pH value. Buffer solutions with various pH ranges can be prepared by the proper selection of these factors.

As exemplary buffer solutions may be mentioned hydrochloric acid-potassium chloride buffer solution (typical pH range: 1-2.2), potassium hydrogenphthalate-hydrochloric acid buffer solution (typical pH range: 2.2-4.0), potassium hydrogenphthalate-sodium hydroxide buffer solution (typical pH range: 4.1-5.9), potassium dihydrogenphosphate-sodium hydroxide buffer solution (typical pH range: 5.8-8), boric acid-sodium hydroxide buffer solution (typical pH range: 8-10.2), sodium hydrogencarbonate-sodium hydroxide buffer solution (typical pH range: 9.6-11) and disodium hydrogen-phosphate-sodium hydroxide buffer solution (typical pH range: 10.9-12). Besides these buffer solutions, various buffer solutions in which the kinds of acid, base or salts constituting these buffer solutions are modified may also be mentioned as examples of the buffer solution.

The pH value of these buffer solutions generally varies depending on the temperature at which it is measured, but, in the process of the present invention, it is represented by their pH value measured at 25° C. for the sake of convenience. In the process of the present invention, aqueous buffer solutions the pHs of which fall within the range of 1-12.5 are preferably used among the aforesaid buffer solutions. In the presence of such a buffer solution, the rhodium compound exhibits a high activity in the synthetis of 2-chloropropionaldehyde from vinyl chloride and the synthesis gas under the co-existence of a trivalent organic phosphorus compound or the oxide of a trivalent organic phosphorus compound.

Further, since the reaction product, 2-chloropropionaldehyde is dissolved in the buffer solution immediately after its formation in a reactor, it is possible to separate it from the organic layer containing vinyl chloride used as a raw material, rhodium and a trivalent organic phosphorus compound or the oxide of a trivalent organic phosphorus compound through liquid-liquid separation. In this case, it is possible to isolate 2-chloropropionaldehyde with ease from the buffer solution containing the 2-chloropropionaldehyde, which has been separated from the raw material of vinyl chloride and the catalyst, by distillation operation or similar means under atmospheric or slightly reduced pressures.

On the other hand, the thus-recovered buffer solution can be utilized repeatedly by extracting it partially and removing from this portion different ions which are by-products of the reaction or replacing it with a fresh buffer solution. Such a process is very favorable as an industrial production process of 2-chloropropionaldehyde.

As the buffer solution useful in the practice of the process of the present invention are particularly preferred those having pH levels in the range of 1-9. A buffer solution in such a pH range is easy to handle industrially and moreover allows the catalyst to exhibit a higher activity. Illustrative of such buffer solutions may include an aqueous solution containing an acid and a slat formed of said acid and a strong base. As the acid, acids the pkas of which are in the range of 0.5-11 are preferred, carboxylic acids being particularly preferred.

Exemplary carboxylic acids may embrace specifically saturated or unsaturated aliphatic mono- or polycarboxylic acids such as formic acid, acetic acid, propionic acid, butyric acid, isobutyric acid, heptanoic acid, acrylic acid, methacrylic acid, crotonic acid, oxalic acid, malonic acid, methylmalonic acid, succinic acid, adipic acid, maleic acid, fumaric acid, 1,2,3-propanetricarboxylic acid, and monovalent or polyvalent aromatic carboxylic acids such as benzoic acid, toluic acid, o-ethylbenzoic acid, 2,4-dimethylbenzoic acid, phthalic acid, isophthalic acid, 3-methylphthalic acid, trimellitic acid, trimesic acid, pyromellitic acid, benzenepentacarboxylic acid and mellitic acid.

Further, carboxylic acids formed by bonding a substituent group such as a halogen atom or an amino or hydroxyl group to an alkyl or aryl group of those carboxylic acids are also preferred. As examples of those carboxylic acids may be mentioned halogen-substituted aliphatic carboxylic acids such as monofluoroacetic acid, difluoroacetic acid, tirfluoroacetic acid, monochloroacetic acid, dichloroacetic acid, trichloroacetic acid, monobromoacetic acid, dibromoacetic acid, 2-chloropropionic acid, 3-chloropropionic acid and 2,2-dichloropropionic acid, halogen-substituted aromatic carboxylic acids such as o-chlorobenzoic acid, m-chlorobenzoic acid, p-chlorobenzoic acid and o-fluorobenzoic acid, amino acids such as glycin, sarcosine, alanine, β-alanine, 4-aminobutyric acid, valine, serine, aspartic acid and glutamic acid, and hydroxycarboxylic acids such as glycolic acid, lactic acid, 2-hydroxybutyric acid, glyceric acid, malic acid, tartaric acid, citric acid, p-hydroxybenzoic acid, salicyclic acid and 2,4-dihydroxybenzoic acid.

Besides, carboxylic acids bonded with substituent groups other than those described above such as phenylacetic acid, pyruvic acid, anisic acid, o-nitrobenzoic acid and cinnamic acid are also mentioned as preferred examples. In the process of the present invention, halogen-substituted aliphatic carboxylic acids and monovalent or polyvalent aromatic carboxylic acids are used particularly preferably among the above-described carboxylic acids.

In the process of the present invention, phosphoric acid, phosphorous acid and, in addition, various oxy acids of phosphorus such as phosphonic acids, phosphonous acids, phosphinic acids and phosphinous acids may also be used favorably as the acid. As illustratives of the oxy acid of phosphorus may be mentioned methylphosphonic acid, ethylphosphonic acid, phenylphosphonic acid, phenylphosphonous acid, dimethylphosphinic acid, diethylphosphinic acid, diphenylphosphinic acid and diphenylphosphinous acid. In addition, boric acid and carbonic acid may also be included in exemplary preferred acids.

As the strong base described above is preferably used the oxide or hydroxide of an alkali metal or alkaline earth metal. Illustratives of the oxide or hydroxide may include magnesium oxide, calcium oxide, strontium oxide, lithium hydroxide, sodium hydroxide, potassium hydroxide, cesium hydroxide, calcium hydroxide, strontium hydroxide and barium hydroxide. Further, guanidines are also favorable strong bases, and specifically various substituted guanidines, for example, methylguanidine and 1,1-dimethylguanidine are illustrated in addition to guanidine. Besides, the preferred strong base may also include various ammonium hydroxides, particularly quaternary ammonium hydroxides. Tetramethylammonium hydroxide, tetraethylammonium hydroxide and choline are mentioned as their specific illustratives.

The salts of the aforesaid acids and bases are obtained by mixing these constituents. However, cases where the same results as in the mixing of an acid and a strong base are obtained, for example, by mixing an acid and the carbonate or hydrogencarbonate of a strong base or by mixing a strong base and the ammonium salt of an acid are also included in the scope of the present invention.

When a polyvalent acid such as phthalic acid or pyromellitic acid is used in the process of the present invention, it is one of the preferable means for the co-existence of an acid and a salt formed of the acid and a strong base to convert a part of the acid radicals to a salt by means of a strong base and allow the rest to remain as free acid. As acids applicable to such a manner, phosphoric acid and phosphorous acid may be cited besides the polycarboxylic acids described above.

In the process of the present invention, it is preferable to use an aqueous buffer solution, but the majority of aromatic polycarboxylic acids have low solubilities to water. However, the above-described means may permit most of the aromatic polycarboxylic acids to improve solubilities in water and form buffer solutions suitable for use in the process of the present invention. In such examples are included isophthalic acid and mellitic acid in addition to phthalic acid and pyromellitic acid. Further, terephalic acid or the like which is not included in the aforesaid exemplary preferred acids may become involved in the exemplary preferred acids by using such a means.

The concentration of the buffer solution is also important in the process of the present invention. When a buffer solution of low concentration is used, nearly the same reaction results as those with a buffer solution of high concentration are obtained in the early stage. However, as the reaction proceeds, pH of the buffer solution is decreased in general, and the activity of the catalyst is impaired when the pH is deviated from a preferred pH range. Therefore, it is generally preferable for the buffer solution to have a higher concentration, but excessively high concentrations are not favored in view of its handling.

As regards the concentration of a buffer solution, it is generally preferable that the concentrations of an acid and a salt constituting the buffer solution are individually in the range of 0.001–10 moles or particularly 0.01–1 mole per liter of the buffer solution. Further, as to the amount of a buffer solution to be used, it is only satisfactory to use a small amount when the buffer solution is of a high concentration, while on the contrary, use of large amounts are favored when it is of a low concentration. It is particularly preferable to select the concentration and amount of a buffer solution in such a way that the pH of the buffer solution after the reaction falls within the range of 1–12.5. Generally, the amount of the buffer solution to be used should preferably be in the range of 0.01–1,000 or particularly 0.1–100 in terms of its weight ratio to the vinyl chloride fed to the reactor as a raw material.

In the process of the present invention, it is carried out more favorably to allow water to co-exist in the reaction system. Such a method makes it possible to improve the activity of the catalyst to a further extent. In the process of the present invention, no particular limitation is vested on the amount of water to be allowed to exist during the reaction. However, the effect of water will be reduced when water is added in an extremely small amount. On the contrary, the use of excessively large amounts also does not improve the reaction results beyond a certain level. Usually, the amount of the water to be used should preferably be in the range of 0.01–1,000 in terms of its weight ratio to the vinyl chloride which is to be fed as a raw material to the reactor. It is particularly preferable to add water at a weight ratio in the range of 0.1–100.

In the process of the present invention, the reaction can proceed without use of any reaction solvent, but usually the reaction is carried out in the presence of a reaction solvent. It is possible to use any reaction solvent unless it affects the reaction adversely. In the process of the present invention, it is preferable to use a water insoluble or hardly soluble solvent as a reaction solvent. By using such a solvent, it is possible to separate with ease the water layer containing the product, 2-chloropropionaldehyde, from the solvent layer containing the catalyst components after the reaction.

The water insoluble or hardly soluble solvent is a solvent the water-solubility of which is not higher than 5 vol.% at its application temperature. A solvent the water-solubility of which is not higher than 0.5 vol.% is particularly preferred. Hydrocarbons are especially preferred as such solvents. Specifically, their illustratives may include saturated hydrocarbons such as hexane, heptane, octane, nonane and decane and aromatic hydrocarbons such as benzene, toluene and xylene. Mixtures of hydrocarbons, such as ligroine, kerosene, light oil and diesel oil which are available industrially, may also be included in such preferred solvents. Besides, ethers sch as dipropyl ether and dibutyl ether, ketones such as diisobutyl ketone and phorone and esters such as butyl butyrate and butyl benzoate may also be mentioned as preferred solvents.

The process of the present invention is usually carried out at a reaction temperature of 10°–150° C. and at a reaction pressure of 10–300 kg/cm² G or preferably 30–150 kg/cm² G. The lower the reaction temperature, the better in view of the thermal stability of the resulting 2-chloropropionaldehyde. For this reason, 20°–80° C. is a particularly preferred temperature range. The mixing molar ratio of carbon monoxide to hydrogen, both of which are used as raw materials, may generally fall within the range of 10–0.1 or preferably 4–0.2. Carbon monoxide and hydrogen may thus be provided as a mixed gas which contains the both components at the aforementioned composition ratio. Water gas may thus be used either as is or as a mixture with a gas inert to the reaction such as methane or nitrogen or with carbon dioxide. The other raw material, vinyl chloride, may be used in a gaseous or liquid form or in the form of a solution having it dissolved in a solvent which is used for the reaction. Although no particular limitation is imposed on the amount of the mixed gas of carbon monoxide and hydrogen used as raw materials, it is preferable to use it in an amount equivalent or more to the vinyl chloride used.

The process of the present invention may be practiced in accordance with any one of the batch, semi-batch or continuous process.

In accordance with the present invention, it is possible to produce 2-chloropropionaldehyde with high selectivity at a low temperature and pressure from vinyl chloride, carbon monoxide and hydrogen used as raw materials.

Particularly, in accordance with the process of the present invention, it becomes possible to produce 2-chloropropionaldehyde in a simple apparatus in an economically beneficial manner without any need for apparatus for the recovery of the base as in the conventional processes or without any concern to the conditions of preventing the loss of the base to a greatest possible extent.

Further, in accordance with the process of the present invention, it is possible to produce 2-chloropropionaldehyde containing impurities which obstract oxidation such as amines in only a very small amount.

Furthermore, in accordance with the process of the present invention, it becomes possible to separate the catalyst components from the reaction product by an industrially preferable means.

The process of the present invention is described more specifically with reference to the following Examples.

EXAMPLE 1

After sweeping with nitrogen gas the interior of an autoclave which was equipped with a stirrer, had an internal volume of 100 ml and was made of stainless steel, the autoclave was charged with 36 mg (0.2 milligram atom as Rh) of hexadecacarbonylhexarhodium, 208 mg (0.8 millimole) of triphenylphosphine, 194 mg (1.5 millimoles) of dichloroacetic acid and 20 g of water, followed by further addition of 20 ml of a toluene solution containing 1.88 g (30 millimoles) of vinyl chloride. A 1:2 (molar ratio) mixed gas of carbon monoxide and hydrogen was then charged under pressure and at room temperature into the autoclave until the interior pressure reached 80 kg/cm² G. Thereafter, the autoclave was raised in temperature to 55° C. at which the contents were reacted for 40 minutes. After cooling the autoclave down to room temperature, the unreacted mixed feed gas was collected in a gas-sampling bag and the autoclave was then opened to take out the liquid reaction mixture containing the catalyst, solvent and reaction product. The gas and liquid were quantitatively analyzed by gas chromatography. As a result, the conversion of vinyl chloride and the yield of 2-chloropropionaldehyde were respectively found to be 32.4% and 8.8 millimoles (a selectivity of 90.5% based on the converted vinyl chloride).

EXAMPLES 2–5

The reaction was carried out in each of the Examples in the same manner as in Example 1 except that the reaction temperature, reaction pressure molar ratio of carbon monoxide to hydrogen and reaction time were changed. The results are summarized in Table 1.

TABLE 1

| Example | Reaction temperature (°C.) | Reaction pressure (kg/cm²G) | Molar ratio of carbon monoxide to hydrogen | Reaction time (min.) | Conversion of vinyl chloride (%) | Selectivity to 2-CPA[*1] (%) |
| --- | --- | --- | --- | --- | --- | --- |
| 2 | 35 | 65 | 1:1 | 600 | 19.8 | 90.8 |
| 3 | 45 | 80 | 2:1 | 60 | 31.5 | 89.4 |
| 4 | 60 | 120 | 1:2 | 30 | 35.2 | 86.4 |
| 5 | 70 | 90 | 1:1 | 10 | 45.2 | 77.8 |

[*1] 2-chloropropionaldehyde

EXAMPLES 6–9

The reaction was carried out in each of the Examples in the same manner as in Example 1 except that the kinds of rhodium compound and trivalent organic phosphorus compound or oxide of trivalent organic phosphorus compound were changed. The amount of the rhodium compound was so adjusted that the amount of rhodium may attain 0.2 milligram atom. The results are shown in Table 2.

TABLE 2

| Example | Rhodium compound | Trivalent organic phosphorus compound or oxide of trivalent organic phosphorus compound (mmol) | Acid (mmol) | Conversion of vinyl chloride (%) | Selectivity to 2-CPA[*1] (%) |
|---|---|---|---|---|---|
| 6 | Hydridocarbonyl-tris(triphenyl-phosphine)-rhodium | Triphenylphosphine oxide (1.0) | Trifluoro-acetic acid (1.0) | 31.9 | 89.2 |
| 7 | Rhodium acetate | Triphenylphosphite (1.5) | Phthalic acid (2.0) | 33.2 | 90.3 |
| 8 | Dodecacarbonyl-tetrarhodium | Tri-n-octyl-phosphine (1.0) | Benzoic acid (2.5) | 21.2 | 89.5 |
| 9 | Dicarbonylacetyl-acetonatorhodium | Tri-n-butyl-phosphine oxide (2.0) | Trimellitic acid (1.5) | 22.7 | 88.1 |

[*1]2-chloropropionaldehyde

EXAMPLES 10–13

The reaction was carried out in each of the Examples in the same manner as in Example 1 except that a different acid or precursor of acid was used in place of dichloacetic acid. The results are summarized in Table 3.

TABLE 3

| Example | Acid or acid precursor (mmol) | Conversion of vinyl chloride (%) | Selectivity to 2-CPA[*1] (%) |
|---|---|---|---|
| 10 | Phthalic anhydride (2.5) | 33.5 | 89.5 |
| 11 | Phenyl-phosphonic acid (2.0) | 31.8 | 91.1 |
| 12 | Phenyl-phosphonous acid (2.5) | 25.9 | 90.8 |
| 13 | Diphenyl-phosphinic acid (0.5) | 21.8 | 87.4 |

[*1]2-chloropropionaldehyde

EXAMPLE 14

The reaction was carried out in the same manner as in Example 1 except for the absence of water.

Analysis revealed a vinyl chloride conversion of 9.8% and a selectivity of 89.1% toward 2-chloropropionaldehyde in the reaction results.

EXAMPLE 15

After sweeping with nitrogen gas the interior of an autoclave which was equipped with a stirrer, had an internal volume of 100 ml and was made of stainless steel, the autoclave was charged with 36 mg (0.2 milligram atom as Rh) of hexadecacarbonylhexarhodium, 157 mg (0.6 millimole) of triphenylphosphine, 82 mg (1 millimole) of sodium acetate and 20 g of water, followed by further addition of 20 ml of a toluene solution containing 3.75 g (60 millimoles) of vinyl chloride. A 1:2 (molar ratio) mixed gas of carbon monoxide and hydrogen was charged under pressure and at room temperature into the autoclave until the interior pressure reached 80 kg/cm$^2$ G. Thereafter, the autoclave was raised in temperature to 60° C. at which the contents were reacted for 20 minutes. After cooling the autoclave down to room temperature, the unreacted mixed feed gas was collected in a gas-sampling bag and the autoclave was then opened to take out the liquid reaction mixture containing the catalyst, solvent and reaction product. The gas and liquid were analyzed quantitatively by gas chromatography. As a result, the conversion of vinyl chloride and the yield of 2-chloropropionaldehyde were respectively found to be 12.6% and 6.6 millimoles (a selectivity of 87.3% based on the converted vinyl chloride).

EXAMPLES 16–20

The reaction was carried out in each of the Examples in the same manner as in Example 15 except that the reaction temperature, reaction pressure, molar ratio of carbon monoxide to hydrogen and reaction time were changed. The results are summarized in Table 4.

TABLE 4

| Example | Reaction temperature (°C.) | Reaction pressure (kg/cm$^2$G) | Molar ratio of carbon monoxide to hydrogen | Reaction time (min.) | Conversion of vinyl chloride (%) | Selectivity to 2-CPA[*1] (%) |
|---|---|---|---|---|---|---|
| 16 | 30 | 120 | 1:4 | 360 | 11.2 | 91.1 |
| 17 | 50 | 40 | 1:1 | 40 | 12.8 | 89.3 |
| 18 | 80 | 90 | 1:3 | 10 | 13.2 | 84.5 |
| 19 | 40 | 40 | 1:5 | 45 | 12.9 | 90.2 |
| 20 | 40 | 100 | 2:1 | 90 | 7.9 | 89.9 |

[*1]2-chloropropionaldehyde

EXAMPLES 21–24

The reaction was carried out in each of the Examples in the same manner as in Example 15 except that the reaction temperature was modified to 55° C. and the kinds of rhodium compound, trivalent organic compound or oxide of trivalent organic phosphorus compound, and oxide, hydroxide or weak acid salt of alkali or alkaline earth metal were changed. The amount of the rhodium compound was so adjusted that the amount of rhodium may attain 0.2 milligram atom. The results are shown in Table 5.

TABLE 5

| Example | Rhodium compound | Trivalent organic phosphorous compound or oxide of trivalent organic phosphorus compound (mmol) | Oxide, hydroxide or weak acid salt of alkali or alkaline earth metal (mmol) | Conversion of vinyl chloride (%) | Selectivity to 2-CPA[*1] (%) |
|---|---|---|---|---|---|
| 21 | Hydridocarbonyl-tris-(triphenylphosphine)rhodium | Triphenylphosphine oxide (1) | Sodium carbonate (1.5) | 11.7 | 87.1 |
| 22 | Dodecacarbonyl-tetrarhodium | Tributylphosphine oxide (2) | Potassium formate (2) | 10.9 | 86.6 |
| 23 | Dicarbonylacetyl-acetonatorhodium | Tri-n-octylphosphine (0.5) | Sodium hydroxide (1) | 8.4 | 81.4 |
| 24 | Rhodium acetate | Triphenylphosphite (2) | Calcium acetate (2) | 10.3 | 88.8 |

[*1] 2-chloropropionaldehyde

EXAMPLE 25

The reaction was carried out in the same manner as in Example 15 except for the absence of water.

Analysis revealed a vinyl chloride conversion of 4.3% and a selectivity of 88.7% toward 2-chloropropionaldehyde in the reaction results.

REFERENCE EXAMPLE 1

A buffer solution was prepared by dissolving 6.25 millimoles of dipotassium phthalate and 6.25 millimoles of monopotassium phthalate in 100 ml of desalted water.

The buffer solution gave a pH value of 4.2 at 25° C.

REFERENCE EXAMPLE 2

A buffer solution was prepared by dissolving 6.25 millimoles of monopotassium phthalate and 6.25 millimoles of phthalic acid in 100 ml of desalted water.

The buffer solution gave a pH value of 2.8 at 25° C.

REFERENCE EXAMPLE 3

A buffer solution was prepared by dissolving 6.25 millimoles of phthalic acid and 6.25 millimoles of sodium hydroxide in 100 ml of desalted water.

The buffer solution gave a pH value of 3.9 at 25° C.

REFERENCE EXAMPLE 4

An aqueous dichloroacetic acid solution having 1 mole of dichloroacetic acid dissolved in 1 liter of desalted water and an aqueous sodium dichloroacetate solution containing 1 mole of sodium dichloroacetate dissolved in 1 liter of desalted water were prepared independently. By mixing the both solutions properly at ratios in the range of 100:1–1:100, three buffer solutions the pH values of which were 1.4, 3.5 and 5.6 were prepared in an individual amount of 100 ml.

REFERENCE EXAMPLE 5

A buffer solution with the pH value adjusted at 11.5 was prepared by adding about 11 ml of an aqueous solution containing 0.1 mole/liter of sodium hydroxide to 50 ml of an aqueous solution containing 0.05 mole/liter of disodium hydrogenphosphate.

EXAMPLE 26

After sweeping with nitrogen gas the interior of an autoclave which was equipped with a stirrer, had an internal volume of 100 ml and was made of stainless steel, the autoclave was charged with 36 mg (0.2 milligram atom as Rh) of hexadecacarbonylhexarhodium, 262 mg (1 millimole) of triphenylphosphine and 20 ml of the buffer solution obtained in Reference Example 1, followed by further addition of 20 ml of a toluene solution containing 1.88 g (30 millimoles) of vinyl chloride. A 1:2 (molar ratio) mixed gas of carbon monoxide and hydrogen was then charged under pressure and at room temperature into the autoclave until the interior pressure reached 100 kg/cm$^2$ G. Thereafter, the autoclave was raised in temperature to 55° C. at which the contents were reacted for 30 minutes. After cooling the autoclave down to room temperature, the unreacted mixed feed gas was collected in a gas-sampling bag and the autoclave was then opened to take out the liquid reaction mixture containing the catalyst, solvent and reaction product. The gas and liquid were analyzed quantitatively by gas chromatography. As a result, the conversion of vinyl chloride and the yield of 2-chloropropionaldehyde were respectively found to be 28.8% and 7.5 millimoles (a selectivity of 86.8% based on the converted vinyl chloride).

EXAMPLES 27–30

The reaction was carried out in each of the Examples in the same manner as in Example 26 except that the reaction temperature, reaction pressure, molar ratio of carbon monoxide to hydrogen and reaction time were changed. The results are summarized in Table 6.

TABLE 6

| Example | Reaction temperature (°C.) | Reaction pressure (kg/cm$^2$G) | Molar ratio of carbon monoxide to hydrogen | Reaction time (min.) | Conversion of vinyl chloride (%) | Selectivity to 2-CPA[*1] (%) |
|---|---|---|---|---|---|---|
| 27 | 30 | 60 | 1:3 | 600 | 18.9 | 89.7 |
| 28 | 45 | 90 | 2:1 | 90 | 29.6 | 88.8 |
| 29 | 60 | 100 | 1:2 | 30 | 33.2 | 84.2 |
| 30 | 70 | 120 | 1:1 | 10 | 41.5 | 74.1 |

EXAMPLES 31–34

The reaction was carried out in each of the Examples in the same manner as in Example 26 except that the reaction temperature and reaction time were respectively modified to 50° C. and 60 minutes and the kinds of rhodium compound, trivalent organic phosphorus compound or the oxide of trivalent organic phosphorus compound and buffer solution were altered. The amount of the rhodium compound was so adjusted that the amount of rhodium may attain 0.2 milligram atom. The results are shown in Table 7.

TABLE 7

| Example | Rhodium compound | Trivalent organic phosphorus compound or oxide of trivalent organic phosphorus compound (mmol) | Buffer solution (20 ml used) | Conversion of vinyl chloride (%) | Selectivity to 2-CPA[*1] (%) |
|---|---|---|---|---|---|
| 31 | Hydridocarbonyl-tris(triphenylphosphine)rhodium | Triphenylphosphine oxide (1.0) | Buffer solution of Reference Example 2 | 25.5 | 87.9 |
| 32 | Dicarbonylacetyl-acetonatorhodium | Tri-n-butylphosphine oxide (2.0) | Buffer solution of Reference Example 3 | 24.8 | 89.0 |
| 33 | Dodecacarbonyl-tetrarhodium | Tri-n-octylphosphine (1.0) | Buffer solution of Reference Example 5 | 16.2 | 87.7 |
| 34 | Rhodium acetate | Triphenylphosphite (1.5) | Buffer solution of Reference Example 1 | 27.9 | 86.5 |

[*1] 2-chloropropionaldehyde

EXAMPLES 35–37

The reaction was carried out in each of the Examples in the same manner as in Example 26 except that the buffer solution was changed to the buffer solution obtained in Reference Example 4 and its amount used was also altered. The results are summarized in Table 8.

TABLE 8

| Example | Amount of buffer solution (ml) | pH value | Conversion of vinyl chloride (%) | Selectivity to 2-CPA[*1] (%) |
|---|---|---|---|---|
| 35 | 30 | 1.4 | 27.6 | 87.8 |
| 36 | 5 | 3.5 | 25.8 | 86.4 |
| 37 | 50 | 5.6 | 35.5 | 89.1 |

[*1] 2-chloropropionaldehyde

What is claimed is:

1. In a process for producing 2-chloropropionaldehyde by reacting vinyl chloride, carbon monoxide and hydrogen in the presence of a rhodium compound and a trivalent organic phosphorus compound or the oxide of a trivalent organic phosphorus compound, the improvement which comprises carrying out the reaction at a temperature of 10° to 150° C. in the presence of:
   (a) at least one acid selected from the group consisting of a halogen-substituted aliphatic carboxylic acid, a monovalent aromatic carboxylic acid, polyvalent aromatic carboxylic acid, a phosphonic acid, a phosphonous acid, a phosphinic acid and a phosphinous acid, or
   (b) at least one compound selected from the group consisting of an oxide of an alkali metal, an oxide of an alkaline earth metal, a hydroxide of an alkali metal, a hydroxide of an alkaline earth metal, a weak acid salt of an alkali metal and a metal acid salt of an alkaline earth metal, or
   (c) a buffer solution.

2. The process as claimed in claim 1 wherein the pH value of the buffer solution is in the range of 1–12.5 at 25° C.

3. The process as claimed in claim 1 wherein the pH value of the buffer solution is in the range of 1–9 at 25° C.

4. The process as claimed in claim 1 wherein the concentration and amount of the buffer solution are so regulated that the pH value of the buffer solution after the reaction may fall wihtin the range of 1–12.5 at 25° C.

5. The process as claimed in claim 1 wherein the buffer solution is an aqueous solution containing an acid the pka of which is in the range of 0.5–11 and a salt formed on the acid and a strong base.

6. The process as claimed in claim 5 wherein the acid is a carboxylic acid.

7. The process as claimed in claim 5 wherein the strong base is the oxide or hydroxide of an alkali metal or alkaline earth metal.

8. The process as claimed in claim 1 wherein the reaction is carried out under the co-existence of a water insoluble or hardly soluble solvent.

9. The process as claimed in claim 1 wherein the reaction is carried out at a temperature of 20°–80° C.

10. The process as claimed in claim 1 wherein the reaction is carried out at a temperature of 10° to 150° C. in the presence of at least one acid selected from the group consisting of dichloroacetic acid, trifluoroacetic acid, phthalic acid, benzoic acid, trimellitic acid, phthalic anhydride, phenylphosphonic acid, phenylphosphonous acid and diphenylphosphinic acid.

11. The process as claimed in claim 1 wherein the reaction is carried out at a temperature of 10° to 150° C. in the presence of at least one compound selected from sodium hydroxide, sodium carbonate, sodium acetate, potassium formate and calcium acetate.

12. The process as claimed in claim 1 wherein the reaction is carried out at a temperature of 10° to 150° C. in the presence of a buffer solution having a pH of 1 to 12.5 at 25° C.

* * * * *